United States Patent
Savage

(10) Patent No.: US 10,111,694 B2
(45) Date of Patent: Oct. 30, 2018

(54) PEDICLE SCREW ASSEMBLY AND METHOD OF ASSEMBLY

(75) Inventor: Daniel S. Savage, Brecksville, OH (US)

(73) Assignee: SKELETAL DESIGN PARTNERSHIP, LLC, Brecksville, OH (US)

( * ) Notice: Subject to any disclaimer, the term of this patent is extended or adjusted under 35 U.S.C. 154(b) by 962 days.

(21) Appl. No.: 13/877,699

(22) PCT Filed: Oct. 5, 2011

(86) PCT No.: PCT/US2011/054931
§ 371 (c)(1),
(2), (4) Date: Apr. 4, 2013

(87) PCT Pub. No.: WO2012/048004
PCT Pub. Date: Apr. 12, 2012

(65) Prior Publication Data
US 2013/0211465 A1    Aug. 15, 2013

Related U.S. Application Data

(60) Provisional application No. 61/390,000, filed on Oct. 5, 2010.

(51) Int. Cl.
*A61B 17/70* (2006.01)
*A61B 17/86* (2006.01)

(52) U.S. Cl.
CPC ...... *A61B 17/8605* (2013.01); *A61B 17/7037* (2013.01); *A61B 17/866* (2013.01); *A61B 17/7032* (2013.01)

(58) Field of Classification Search
CPC ............ A61B 17/7032; A61B 17/7035; A61B 17/7037; A61B 17/866; A61B 17/8605;
(Continued)

(56) References Cited

U.S. PATENT DOCUMENTS 5,885,286 A * 3/1999 Sherman ............ A61B 17/7037
606/266
6,248,105 B1   6/2001 Schlapfer et al.
(Continued)

FOREIGN PATENT DOCUMENTS

DE          19720782 A1   11/1998
DE      102005005647 A1    8/2006
(Continued)

OTHER PUBLICATIONS

International Search Report for PCT/US2011/054931 dated Apr. 27, 2012.
(Continued)

*Primary Examiner* — Zade Coley
*Assistant Examiner* — Jessica Weiss
(74) *Attorney, Agent, or Firm* — Heslin Rothenberg Farley & Mesiti P.C.

(57) ABSTRACT

A pedicle screw assembly and method of assembly are disclosed. The pedicle screw assembly includes a bone fastener having a head at a proximal end and a threaded portion extending between the proximal end and a distal end. The assembly also includes a compression member having a conical inner surface and a locking member having an outer surface adapted to mate with the conical inner surface of the compression member. The assembly may also have an elongated member and a set screw that has a threaded portion. The assembly may also have a receiving housing having a central bore extending from a threaded proximal end to a distal end and a U-shaped cavity positioned perpendicular to the central bore and configured to receive the elongated member.

24 Claims, 14 Drawing Sheets

(58) Field of Classification Search
CPC ............ A61B 17/7005; A61B 17/7007; A61B 17/7008; A61B 17/7043
USPC ................................. 606/246–278, 300–321
See application file for complete search history.

(56) References Cited

U.S. PATENT DOCUMENTS

| | | |
|---|---|---|
| 2007/0118123 A1 | 5/2007 | Strausbaugh et al. |
| 2007/0233087 A1 | 10/2007 | Schlapfer |
| 2008/0154315 A1 | 6/2008 | Jackson |
| 2008/0269809 A1 | 10/2008 | Garamszegi |
| 2009/0143827 A1* | 6/2009 | Levy .................. A61B 17/7037 606/308 |
| 2009/0204155 A1* | 8/2009 | Aschmann ......... A61B 17/7032 606/264 |
| 2010/0152787 A1* | 6/2010 | Walsh ................ A61B 17/7037 606/308 |
| 2013/0096620 A1* | 4/2013 | Biedermann .......... A61B 17/70 606/279 |

FOREIGN PATENT DOCUMENTS

| | | |
|---|---|---|
| EP | 1741396 A1 | 10/2007 |
| WO | 2009/107901 A1 | 9/2009 |

OTHER PUBLICATIONS

International Preliminary Report on Patentability for corresponding PCT application No. PCT/US2011/054931, dated Apr. 18, 2013.
Dec. 23, 2014: Supplementary European Search Report for European Application No. 11831520.9.

\* cited by examiner

PEDICLE SCREW ASSEMBLY AND METHOD OF ASSEMBLY

CROSS REFERENCE TO RELATED APPLICATION

This application is a national stage filing under section 371 of International Application No. PCT/US2011/054931 filed on Oct. 5, 2011, and published in English on Apr. 12, 2012 as /WO 2012/048004 A2 and claims priority to U.S. provisional patent application No. 61/390,000 filed on Oct. 5, 2010, the entire disclosure of applications being hereby incorporated by reference.

TECHNICAL FIELD

This invention relates generally to the field of surgical implants, and more specifically, to the field of spine fixation devices and assemblies.

BACKGROUND OF THE INVENTION

Spinal fixation assemblies may be used to align and/or fix a desired relationship between adjacent vertebrae. Such assemblies generally include a connecting rod that is attached to a plurality of vertebral bodies by an anchoring device which may include hooks, bolts, wires, or screws. The connecting rod can have a predetermined shape or contour that has been designed according to the properties of the target implantation site, and once installed, the rod secures the plurality of vertebral bodies in a specific spatial relationship to allow bone fusion to occur.

Spinal rods can be anchored to various anatomic aspects of the vertebral bodies, but because of the size and contour variances seen in the spine, a variety of anchoring devices have been developed and are commercially available. Pedicle screw assemblies are an example of an anchoring device and typically include a bone screw that has a threaded shank and a head portion that is connected in some manner to a receiving element. The receiving element may include a portion that is usually in the form of a U-shaped slot that accepts a connecting rod. A threaded set-screw or cap may be used to lock the rod into the receiving element that is coupled to the bone screw.

In order to clinically address the vertebral size and anatomic differences seen within the various portions of the spinal column, pedicle screw systems that are used currently frequently incorporate designs that require complex assembly steps which increase the cost of manufacturing and difficulty with intraoperative assembly. In addition, current pedicle screw system designs typically require a high tightening torque to achieve an adequate lock on the bone screw implants. As a result of the high tightening torque force requirements, larger implant profiles may be necessary to withstand the resultant loads and cause disruption or fracture at the screw-bone interface. Further, a continuing unsolved problem exists with previous pedicle screw designs with the splaying or separation of receiving element or housing when a top screw or threaded member is threaded into or engaged with the housing to apply an adequate load to the rod that is being held within the housing.

Accordingly, there remains a need for a pedicle screw assembly that is bottom loading to allow for adequate fixation of the rod to the receiving element while not disrupting the bone-bone screw interface during implantation or splaying of the receiving element when set screw securement occurs.

SUMMARY OF THE INVENTION

Advancement of the state of pedicle screw assemblies is believed desirable. This disclosed embodiment is designed to allow for adequate securement of an elongated member to a receiving housing without compromising the bone-bone screw interface that may occur when a high torque is placed onto the set screw during intraoperative assembly. Further, the disclosed pedicle screw assembly utilizes a novel receiving housing/locking member/collet and compression member arrangement that reduces the splaying forces that are intrinsic with a set screw on elongated member locking interface. The reduction in splaying forces, even at high torque loads, allows the receiving housing to be constructed with a lower outside profile.

The invention provides, in one aspect a pedicle screw assembly that includes a bone fastener having a head at a proximal end and a threaded portion that extends between the proximal end and a distal end. The assembly may also include a compression member having a cylindrical outer surface and a conical inner surface. The assembly may further include a locking member having an outer surface adapted to mate with the conical inner surface of the compression member and a receiving housing that has a central bore extending from a proximal end to a distal end with the distal end having a first opening sized to receive the head of the bone fastener and the proximal end having a second opening sized to receive the locking member and the compression member.

Another embodiment of the invention is a method of assembling the pedicle screw system. The method may include the step of proximally inserting the locking member into the central bore of the receiving housing. The method may also include the step of inserting the head of a bone fastener through a distal opening of the central bore of the receiving housing to operationally couple with the locking member. A further step may be seating the locking member in a distal portion of the central bore that is proximate to the distal opening. The method may also include the steps of proximally inserting a compression member into the central bore of the receiving member and then positioning the internal conical surface of the compression member adjacent to an external conical surface of the locking member.

Further additional features and benefits will become apparent from the attached drawings and following descriptions of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

DETAILED DESCRIPTION FOR CARRYING OUT THE INVENTION

Figure 1:
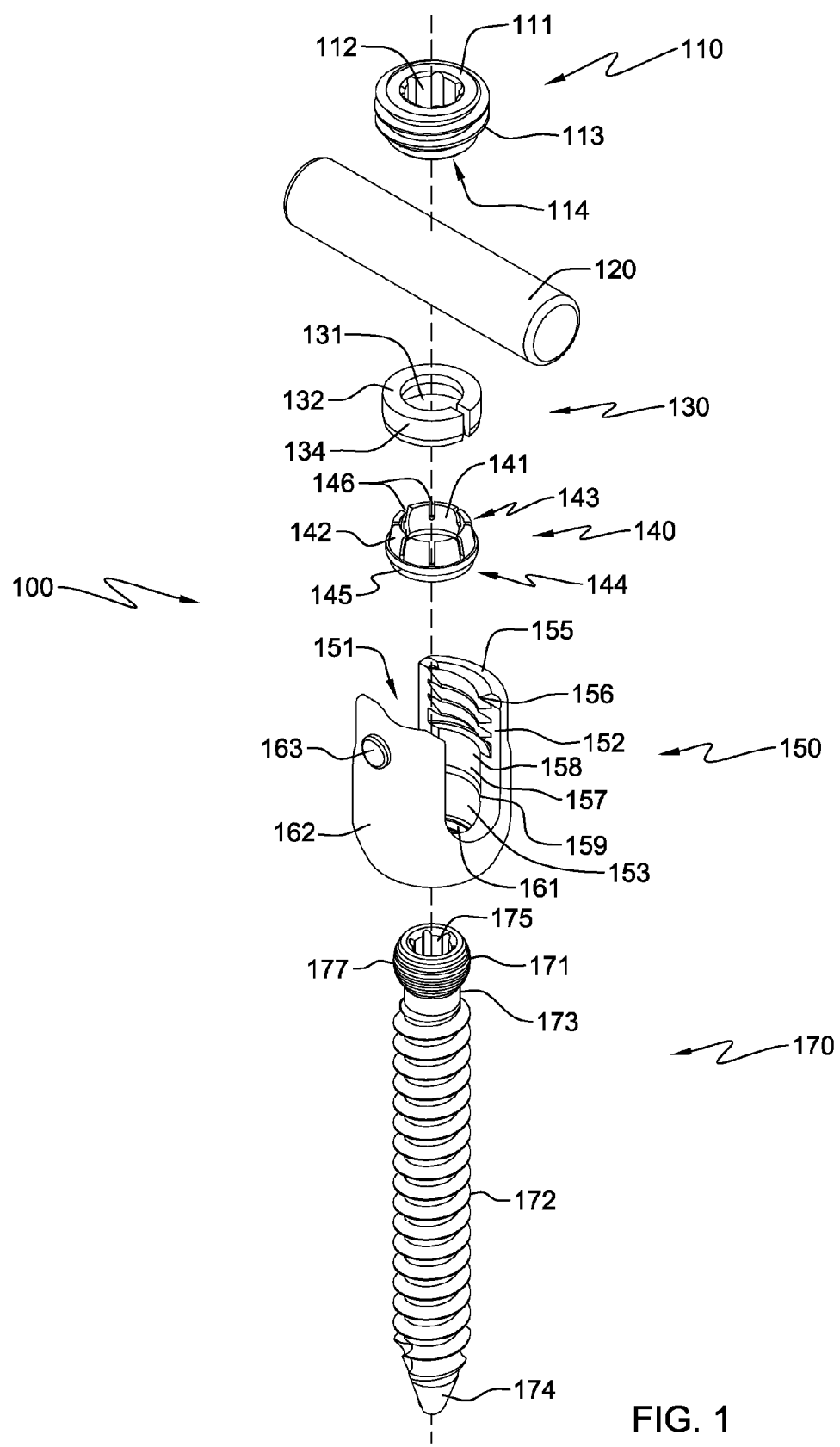
FIG. 1 is an exploded view of one embodiment of a pedicle screw assembly, in accordance with an aspect of the present invention.

For the purposes of promoting an understanding of the principles of the pedicle screw assembly, reference will now be made to the embodiments, or examples, illustrated in the drawings that have been attached hereto and specific language will be used to describe these. It will nevertheless be understood that no limitation of the scope of the invention is thereby intended. Any alterations and further modifications in the described embodiments, and any further applications of the principles of the invention as described herein are contemplated as would normally occur to one skilled in the art to which the pedicle screw assembly invention relates.

In this detailed description and the following claims, the words proximal, distal, anterior, posterior, medial, lateral, superior and inferior are defined by their standard usage for indicating a particular part of a surgical implant according to the relative disposition of the surgical implant or directional terms of reference. For example, "proximal" means the portion of the surgical implant positioned nearest the torso while "distal" indicates the part of the surgical implant farthest from the torso. As for directional terms, "anterior" is a direction towards the front side of the body, "posterior" means a direction towards the back of the body, "medial" means towards the midline of the body, "lateral" is a direction towards the sides or away from the midline of the body, "superior" means a direction above, and "inferior" means a direction below another object or structure. In addition, for the purposes of this disclosure when referencing the components and the assembly, the term "proximal" may also mean the portion of the component or assembly that is closest or nearest an insertion instrument. The term "distal" may mean the portion of the component or assembly that is farthest away from the insertion instrument.

Generally stated, disclosed herein is a pedicle screw assembly for use to secure an elongated member, for example a rod, to adjacent vertebral bodies. The pedicle screw assembly typically has a set screw or retaining member, an elongated member, a compression member, a locking member, a receiving housing and a bone fastener, which may be in the form of a bone screw. Also, described herein is a method of assembly of the pedicle screw system, which includes the bottom or distally loading of the bone fastener into the central bore of a receiving housing. The invention or assembly will generally be referred to herein as a "pedicle screw assembly," a "pedicle screw system," or simply an "assembly" or "a system" for ease of discussion.

Figure 2:
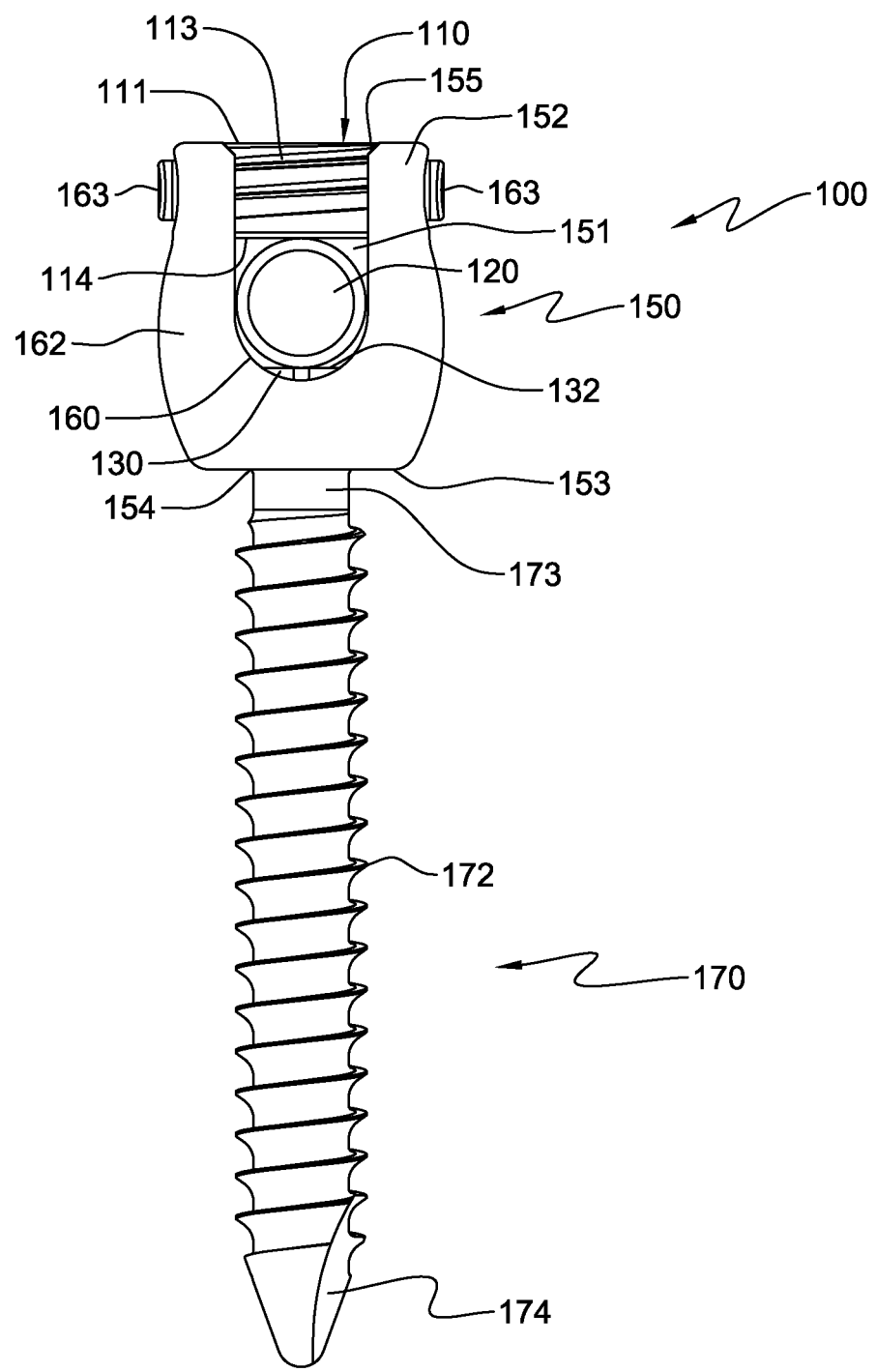
FIG. 2 is a side view of the pedicle screw assembly of FIG. 1, in accordance with an aspect of the present invention.

FIG. 1 shows the general arrangement of a pedicle screw assembly 100 in accordance with an aspect of the present invention. Assembly 100 includes, generally, a set screw or retaining member 110, an elongated member 120, a compression member 130 and locking member 140 and receiving housing 150 and a bone fastener 170. As seen in FIGS. 1 and 2, set screw 110 is generally cylindrical in shape and includes a top surface 111 that may have an internal drive feature 112 which may be hex or hex lobe in shape to mate with a corresponding insertion or driver tool. As see in FIG. 1, set screw 110 has screw threads 113 disposed on its outer surface that match the internal thread pattern of receiving housing 150. Typically, because of the large torsional loads that may be applied to set screw 110, standard buttress threads may be used, although other thread patterns may also be used depending up on the clinical application of the assembly. Set screw 110 also may include a bottom surface 114 that will contact elongated member 120 when tightened. Set screw 110 applies a compressive force that is transmitted through assembly 100 to secure bone fastener 170 in a specific position. Bottom surface 114 is seen as being planar, although other geometric configurations may be utilized to maximize force transmission and eliminate point loading at the bottom surface-elongated member interface.

As seen in FIGS. 1-5, assembly 100 may include an elongated member 120 that has a length that spans over the vertebral bodies to which the assembly 100 is secured. Elongated member 120 is shown as a rod that may be fabricated from generally accepted bio-inert materials including but not limited to stainless steel, titanium, cobalt chromium, shape memory metal and other bio-compatible metal alloys. Also, elongated member 120 may be fabricated from certain bio-inert polymers and composites, including but not limited to carbon fiber composites to provide flexibility within the construct. Elongated member 120 may also be in the form of a cable or other similar cylindrical structure. Although elongated member 120 is seen to have a circular cross-sectional geometry, other geometries may be utilized so long as the diameter or cross-section is sized to fit with the U-shaped channel 160 (see FIG. 2) of receiving housing 150.

Figure 5:
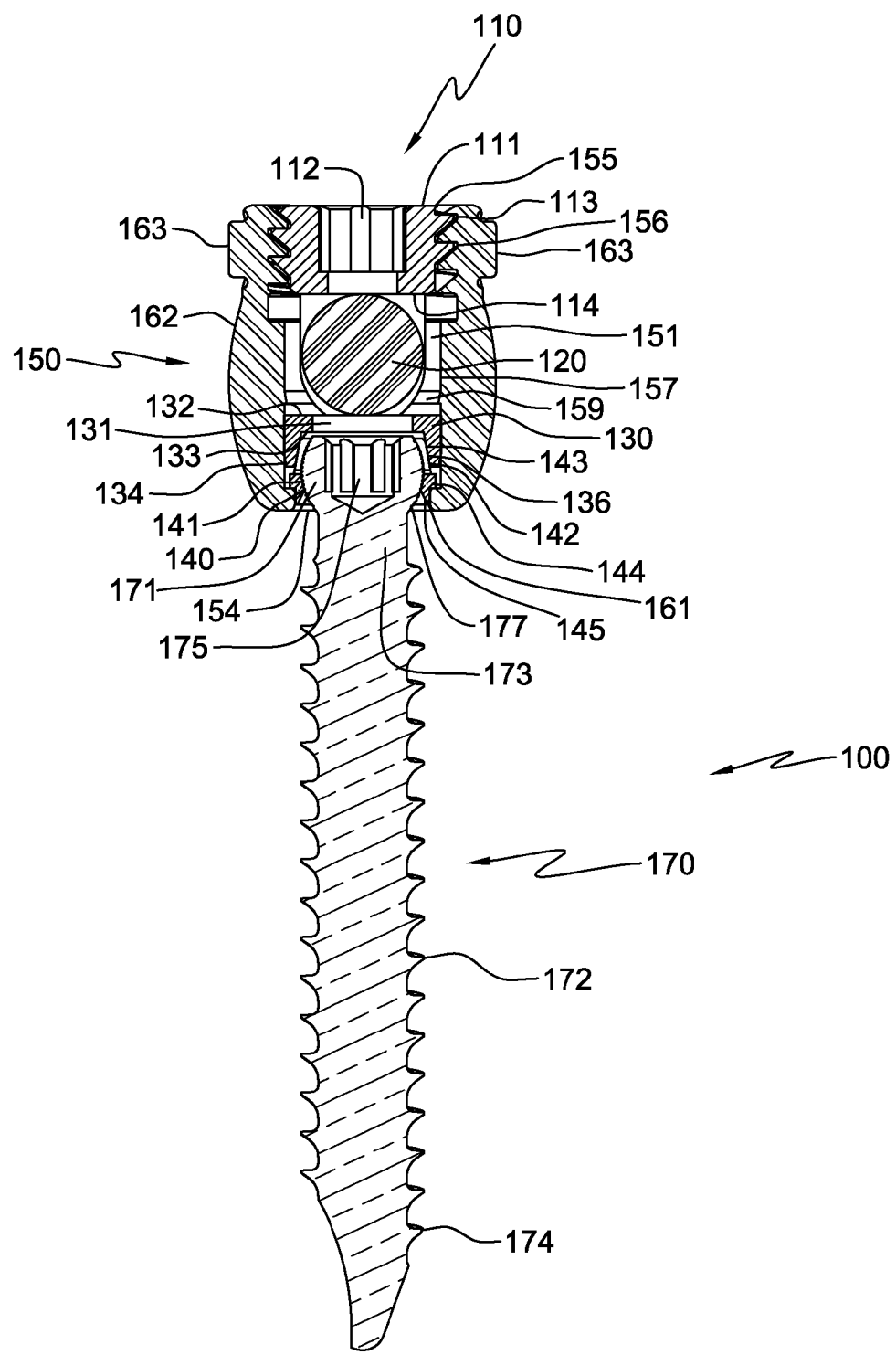
FIG. 5 is a cross-sectional view of the pedicle screw assembly of FIG. 1, in accordance with an aspect of the present invention.
Figure 12A:
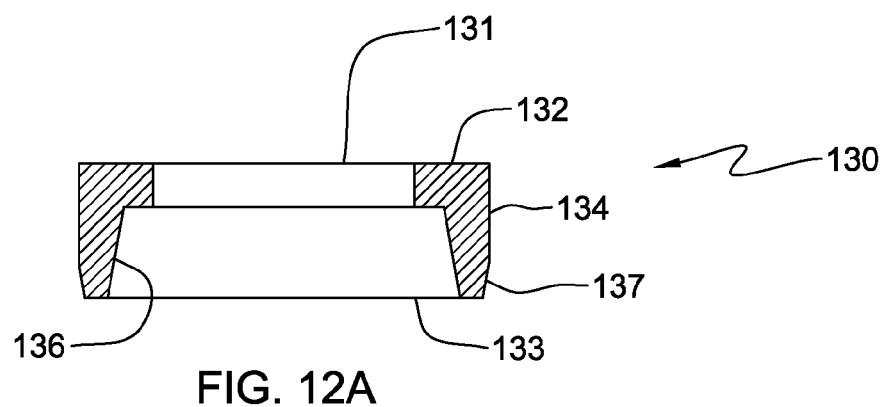
FIG. 12A is an enlarged sectional view of a compression member of the pedicle screw assembly of FIG. 1, in accordance with an aspect of the present invention.

FIGS. 1 and 12A show compression member 130 has being generally cylindrical in nature, with a through hole 131 at the center. Through hole 131 would permit the use of a drive or removal instrument to pass through compressive member 130 and interface directly with bone fastener 170. Compression member 130 also includes an upper or top surface 132 that will contact the bottom aspect of elongated member 120 when assembly 100 is constructed. Top surface 132 is seen in FIGS. 1 and 12A as being planar. It is further contemplated that, although not shown, top surface 132 may include a depression to form an arcuate surface that will result in more surface contact between compression member 130 and elongated member 120 when assembly is loaded by set screw 110. The sectional view seen in FIGS. 5 and 12A show that the lower or bottom surface 133 of compression member 130 as being generally planar. The planar orientation facilitates the seating of compression member 130 within the central bore 151 of receiving housing 150.

Also seen in FIG. 12A is the conical inner surface 136 of compression member 130. Conical inner surface 136 includes a draft angle that corresponds to the taper angle of the conical outer surface 142 of locking member 140. Conical inner surface 136 is designed and configured to interact and engage with conical outer surface 142 of locking member 140 to facilitate the load transfer between these two elements when a compressive force is applied by the tightening of set screw 110 during the assembly process. The taper angles of conical inner surface 136 and conical outer surface 142 allow for surface contact between the two elements when seated relative to each other and diminish potential point loading.

Compression member 130 also has a smooth cylindrical outer surface 134 that assists the assembly process as compression member 130 is inserted into central bore 151 proximally and is initially positioned within the intermediate portion 157 of receiving housing 150. FIG. 12A also shows a chamfer or relief 137 at the distal end of compression member 130. Chamfer 137 facilitates the passage of compression member 130 over the retention mechanism 159 located on the inner surface 158 of intermediate portion 157 of receiving housing 150. (See FIG. 11A) The functionality of retention mechanism 159 will be discussed in more detail below.

Figure 12B:
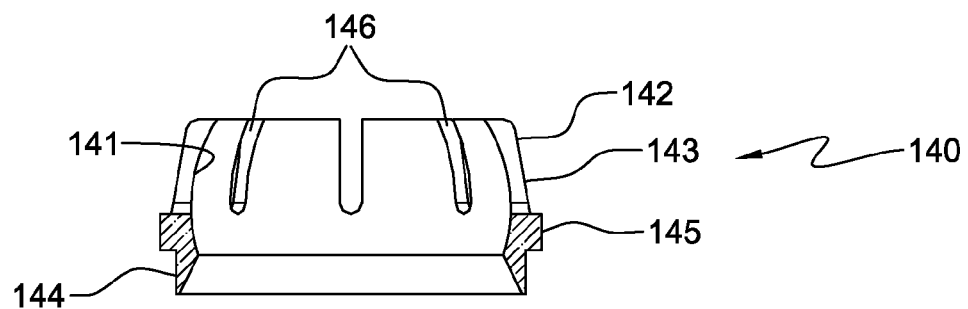
FIG. 12B is an enlarged sectional view of the locking member of the pedicle screw assembly of FIG. 1, in accordance with an aspect of the present invention.

FIGS. 1, 5 and 12B show locking member 140 which functions to encapsulate and hold the spherical head 171 of bone fastener 170 when a compressive load is applied to compression member 130. As seen in FIG. 12B, the inner surface 141 of locking member 140 is spherically shaped relative to the central axis of assembly 100. Spherical inner surface 141 is configured to mate with the corresponding spherical head 171 of bone fastener 170. One skilled in the art would appreciate that many shape variations could be used (e.g. cylindrical and conical) both for the head of bone fastener 170, and the inner surface of locking member 140. In order to operate properly, if a different shape is used in the assembly, the inner surface of locking member 140 will need to match the head shape of bone fastener 170.

The outer surface 142 of locking member 140 in the proximal portion 143 is conically shaped to match the conically shaped inner surface 136 of compression member 130 when the two components are mated together. Conical outer surface 142 tapers out from the top aspect to the bottom aspect of locking member 140, such that the top edge of conical outer surface 142 is smaller in diameter than the bottom edge of conical outer surface 142.

As seen in FIG. 12B, a circumferential flange 145 is positioned at the distal portion 144. Flange 145 may interface or engage with the bottom of the first opening or distal opening 154 in receiving housing 150. Flange 145 may also function to keep locking member 140 from falling through first opening 154 and out of central bore 151. Locking member 140 is generally anticipated to be a single component with material removed in multiple locations to permit elastic deformability, either expandability or compressibility. More specifically, as seen in FIGS. 1 and 12B, proximal portion 143 includes several vertically oriented slots 146 that allow for the elastic expansion of spherical inner surface 141 when spherical head 171 is advanced into locking member 140 from a distal or bottom direction. One skilled in the art will appreciate that such expansion of locking member 140 may be accomplished by other mechanical means through other various oriented relief placement, as well as by fabricating locking member 140 out of a tough and elastically deformable material. The expandability of proximal portion 143 and spherical inner surface 141 allows locking member 140 to receive a larger diameter bone fastener head than the non-expanded sized spherical inner surface 141. Having the ability to expand will facilitate maximum surface contact between spherical inner surface 141 and spherical head 171 following placement within locking member 140.

Figure 3:
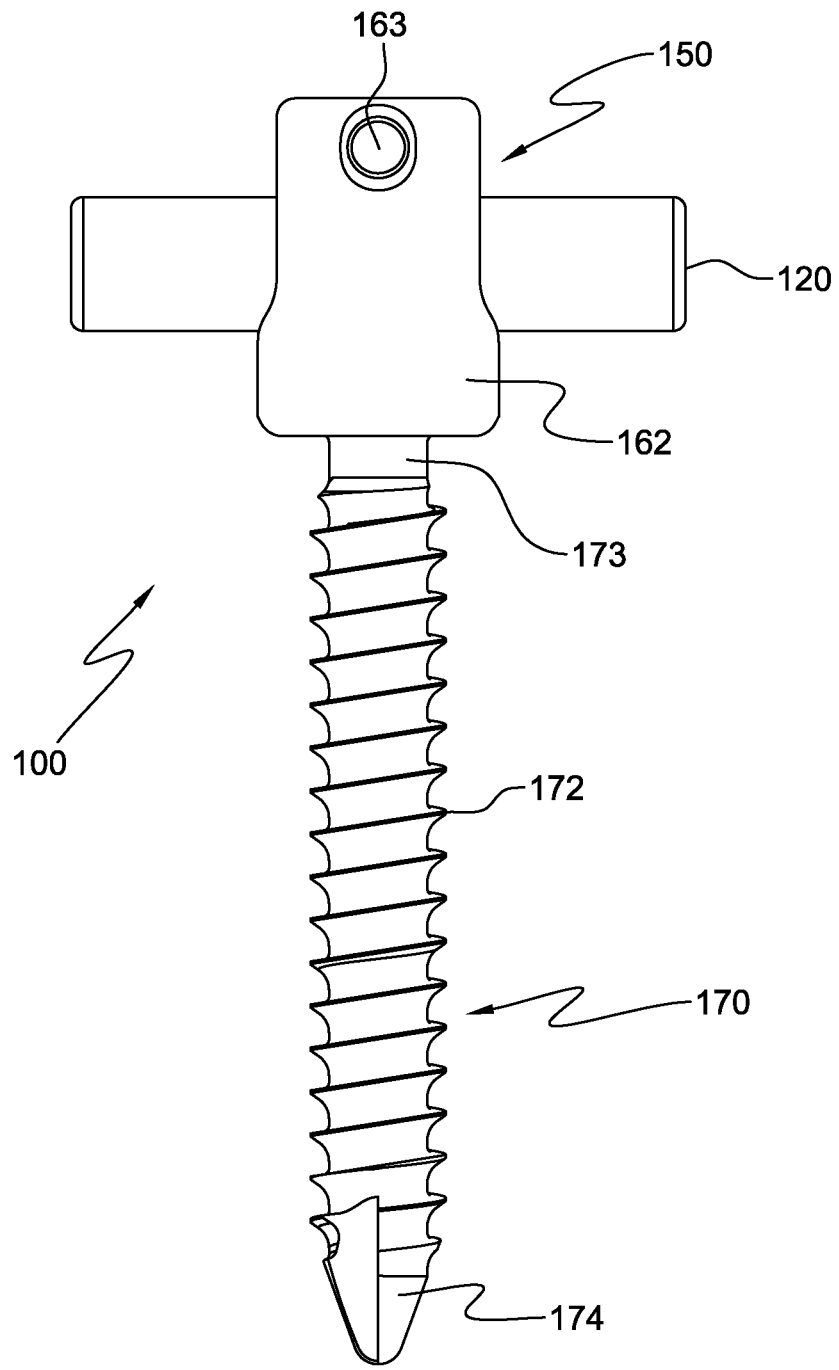
FIG. 3 is a lateral view of the pedicle screw assembly of FIG. 1, in accordance with an aspect of the present invention.
Figure 4:
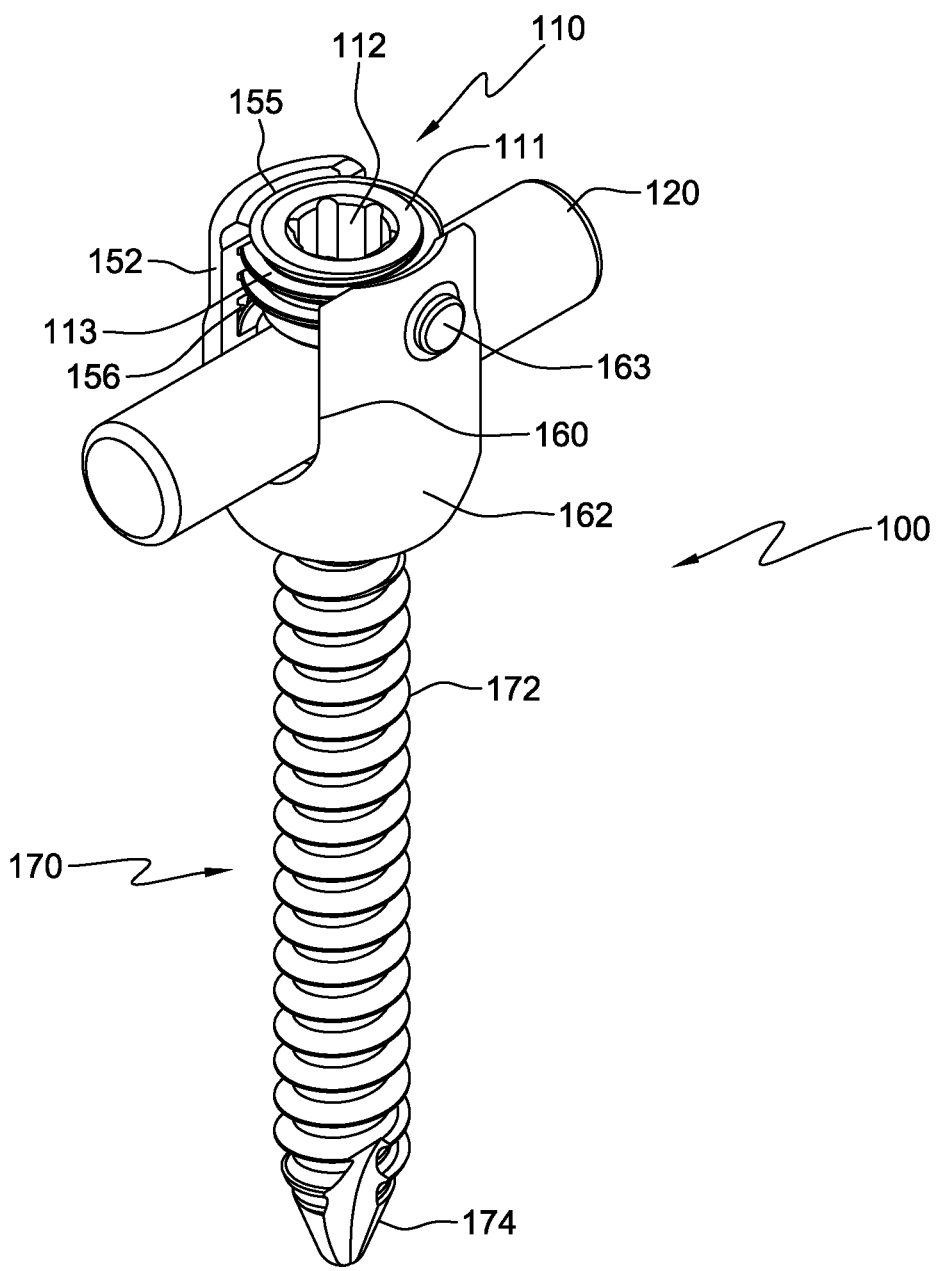
FIG. 4 is a top, perspective view of the pedicle screw assembly of FIG. 1, in accordance with an aspect of the present invention.

As seen in FIGS. 2 and 3, receiving housing 150 has a generally tulip-like shaped outer profile with at least two horizontally oriented bosses or hubs 163 extending away from the outer surface 162. Bosses or hubs 163 are oriented to facilitate the connection of an insertion instrument that may be using during an open or minimally invasive surgical procedure.

Figure 11A:
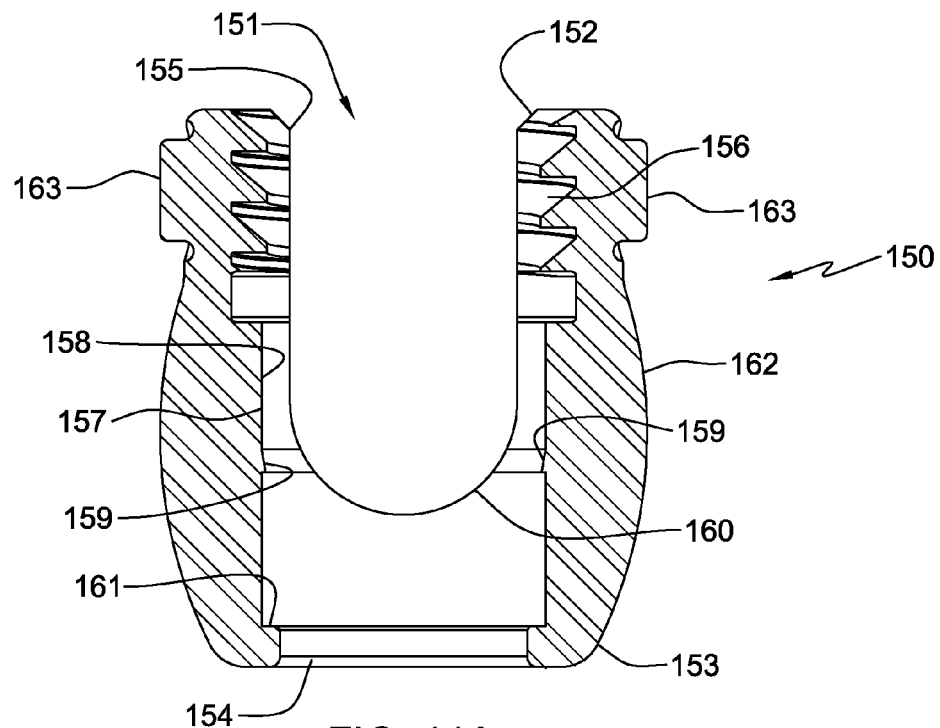
FIG. 11A is an enlarged sectional view of a receiving housing of the pedicle screw assembly of FIG. 1, in accordance with an aspect of the present invention.

FIGS. 5 and 11A are sectional views of receiving housing 150 and show central bore 151 extending throughout, from the proximal end 152 to the distal end 153. First opening or distal opening 154 is a hole that is located at the bottom or distal end 153 of receiving housing 150 and is sized to receive spherical head 171 when assembly 100 is being constructed. A second opening or proximal opening 155 is located at proximal end 152 and is configured to receive locking member 140, compression member 130, elongated member 120 and set screw 110. Oriented perpendicular to central bore 150 is transverse U-shaped channel 160 that extends from one side of receiving housing 150 to the opposite side. U-shaped channel 160 is configured to receive elongated member 120 during the assembly of system 100.

Also shown in FIGS. 5 and 11A, threads 156 are located on the inner surface of central bore 151 in proximal end 152. Threads 156 are the same as the corresponding threads 113 of set screw 110, which for example purposes are shown to be buttress threads. Threads 156 extend for a limited length within central bore 151 to avoid interference with inserted elongated member 120 following seating at the base of U-shaped channel 160. Intermediate portion 157 extends between proximal end 152 and distal end 153 and typically has a smooth inner surface 158 to facilitate the placement of compression member 130 and locking member 140 along central bore 151. Disposed on inner surface 158 is retention mechanism 159 that is shown in FIG. 11A for example purposes to be a circumferential ramped barb or projection. Other shaped circumferential projections or incremental tabs may be used as well. Retention mechanism 159 functions to keep compression member 130 positioned in distal end 153 of receiving housing 150 when low or no compressive loads are being applied by set screw 110. In operation, locking member 140 is advanced first through second opening or proximal opening 155 into central bore 151 to a position in distal end 153. Compression member 130 typically has a larger outer diameter than locking member 140 is then placed into central bore 151 through second opening 155 and advanced into intermediate portion 157. Chamfer 137 facilitates the passage of compression member 130 over retention mechanism 159 to a position below or more distal to retention mechanism 159. The projection or ridge that comprises retention mechanism 159 extends towards the center of central bore 151 and acts to keep compression member 130 below retention mechanism 159 because the larger diameter of compression member 130 cannot move past the narrower diameter that has been created by retention mechanism 159.

As seen in FIG. 11A, the diameter of central bore 151 decreases distally to create a circumferential ledge or shelf 161 proximate to first opening or distal opening 154. Ledge 162 engages flange 145 of locking member 140 to securely seat locking member 140 at distal end 153. Seating locking member 140 will prevent locking member 140 from expanding and releasing spherical head 171 once positioned adjacent spherical inner surface 141.

FIG. 1 further shows bone fastener 170 before insertion into first or distal opening 154 of receiving housing 150. For example purposes, bone fastener 170 is shown as a bone screw, although one skilled in the art will appreciate that many different types of bone fasteners may be used, including but not limited to pins, rods and hooks. Bone fastener 170 has a proximal end 173 and a distal end 174 with an intermediate threaded portion 172. Threaded portion 172 typically will have cancellous threads to maximize bone thread contact to increase pullout strength. Distal end 174 may also include a self-tapping tip to facilitate insertion into the bone. Bone fastener 170 also includes a spherical head 171 that extends from proximal end 173. Included within spherical head 171 may be a female or internal drive opening 175 that receives a tip of a screw driver or like insertion tool. The configuration of internal drive opening 175 may be for example, a hex or hex lobe. Spherical head 171 also has a spherical outer surface 177. Surface 177 will typically be textured or roughened in some manner, including have a blast finish or slight circumferential ridges. The surface texturing assists with the securement of spherical head 171 within locking member 140 following placement of spherical surface 177 in contact with spherical inner surface 141 of locking member 140. As a result of the alignment of spherical head 171 within locking member 140, bone fastener 170 does not interact or come in contact with receiving housing 150 or elongated member 120 in any manner. As noted above, it is contemplated that other shaped heads for bone fastener 170 may be used for certain clinical situations. These shapes could include a cylinder, conical, oval, and tubular. In the event that an alternative shape is used for the head of bone fastener 170, the inner surface of locking member 140 will need to match the alternative shape in order to maximize surface contact and securement between locking member 140 and bone fastener 170.

FIGS. 6-10, 11B, 13A and 13B further show an alternative embodiment of the pedicle screw assembly. Many of the structural elements included in the alternative embodiment mirror the functionality of the structural elements disclosed above, although different reference numbers have been used to identify these elements.

Figure 6:
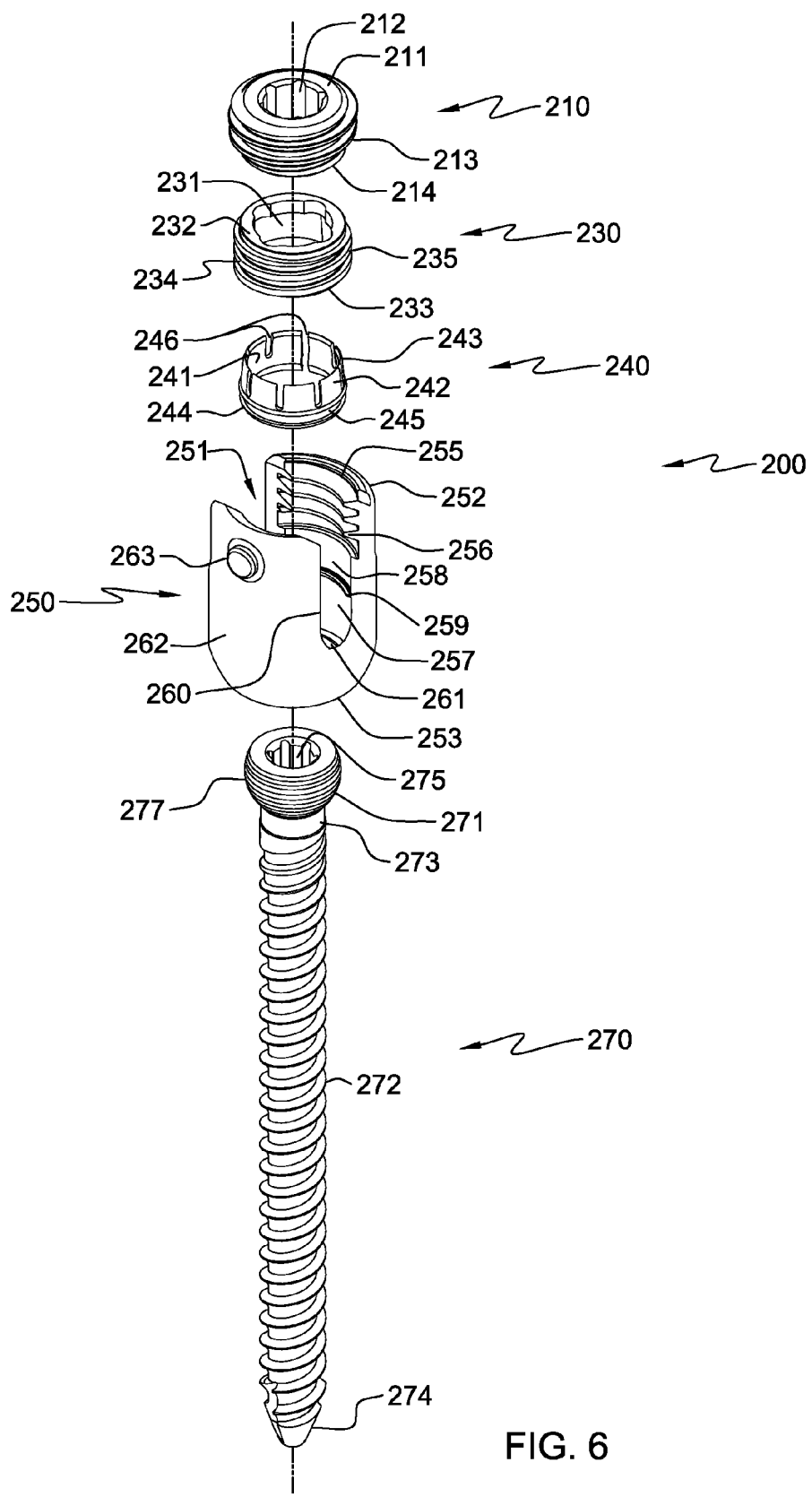
FIG. 6 is an exploded view of an alternative embodiment of a pedicle screw assembly, in accordance with an aspect of the present invention.
Figure 9:
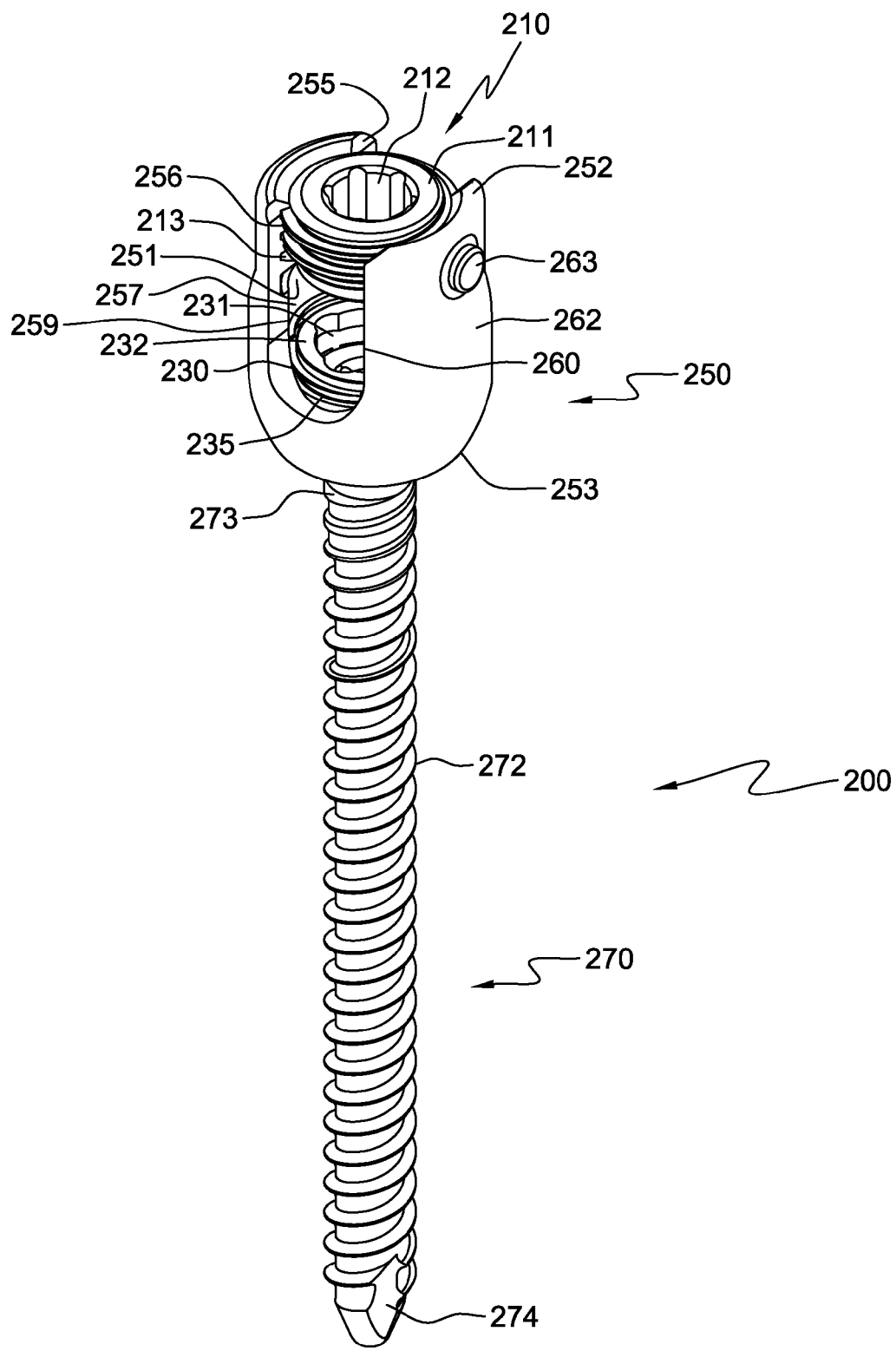
FIG. 9 is a top, perspective view of the pedicle screw assembly of FIG. 6, in accordance with an aspect of the present invention.

FIG. 6 shows the general arrangement of an alternative embodiment of a pedicle screw assembly 200 in accordance with an aspect of the present invention. Assembly 200 includes, generally, a set screw or retaining member 210, a compression member 230, a locking member 240, a receiving housing 250 and a bone fastener 270. As seen in FIGS. 6 and 9, set screw 210 is generally cylindrical in shape and includes a top surface 211 that may have internal drive feature 212 which for example purposes may be hex or hex lobe in shape to mate with a corresponding insertion or driver tool. Also seen in FIG. 6, set screw 210 has screw threads 213 disposed on its outer surface that match the internal thread pattern of receiving housing 250. Typically, because of the large torsional loads that may be applied to set screw 210 standard buttress threads may be used, although other thread patterns are contemplated depending on the clinical application of the assembly 200. Set screw 210 also may include a bottom surface 214 that will contact an elongated member when tightened. Set screw 210 applies a compressive force that is transmitted through assembly 200 to secure bone fastener 270 in a specific position. Bottom surface 214 is seen as being planar, although other geometric configurations may be utilized to maximize force transmission and eliminate point loading at the bottom surface-elongated member interface.

It should be understood that assembly 200 will include an elongated member similar to element 120 as seen in FIGS. 1-5 above. For the sake of clarity in showing assembly 200, elongated member has not been included in FIGS. 6-10, although it is understood that an elongated member will be an element of assembly 200 and will have the same functional and structural characteristics as described for elongated member 120 above.

Figure 10:
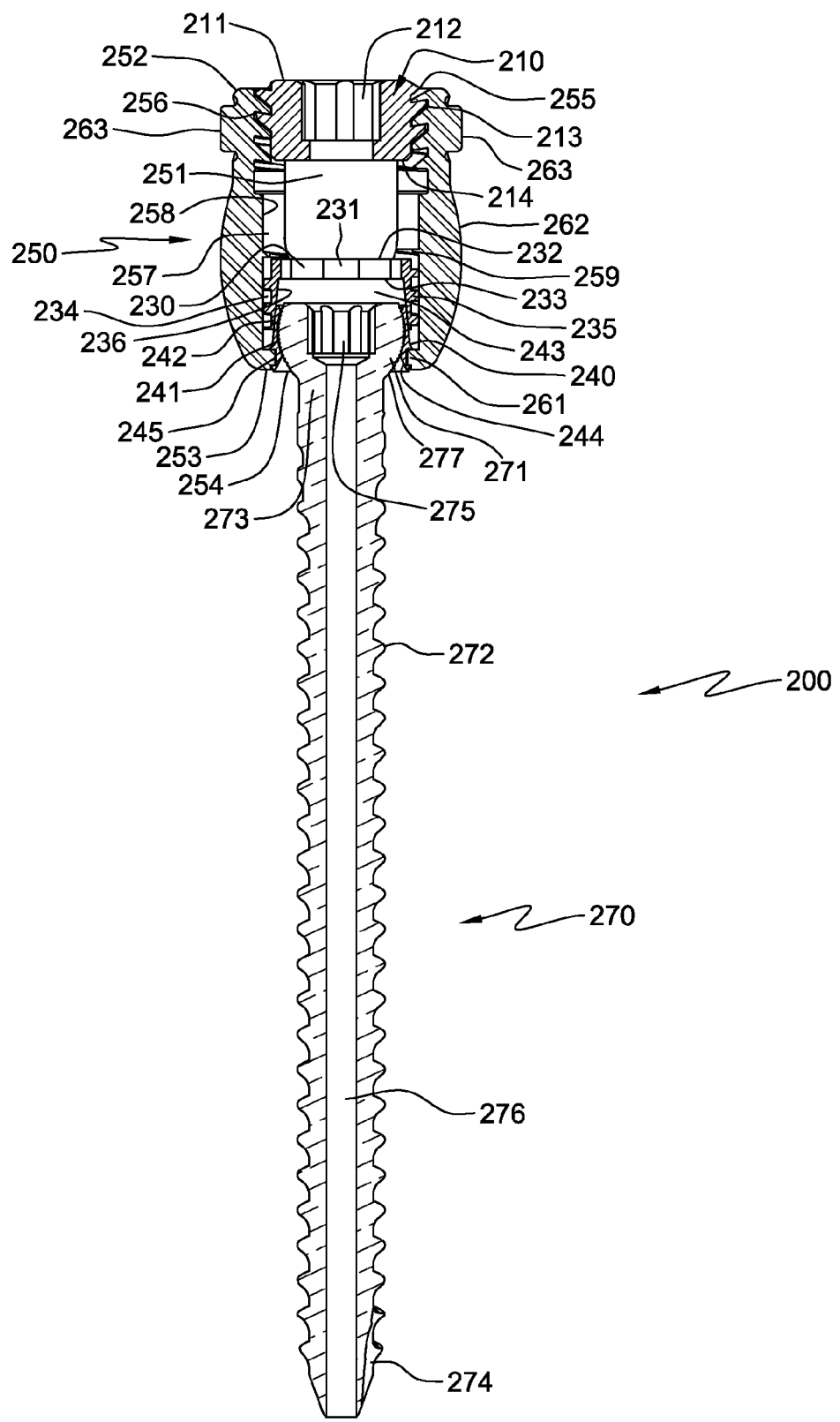
FIG. 10 is a cross-sectional view of the pedicle screw assembly of FIG. 6, in accordance with an aspect of the present invention.
Figure 13A:
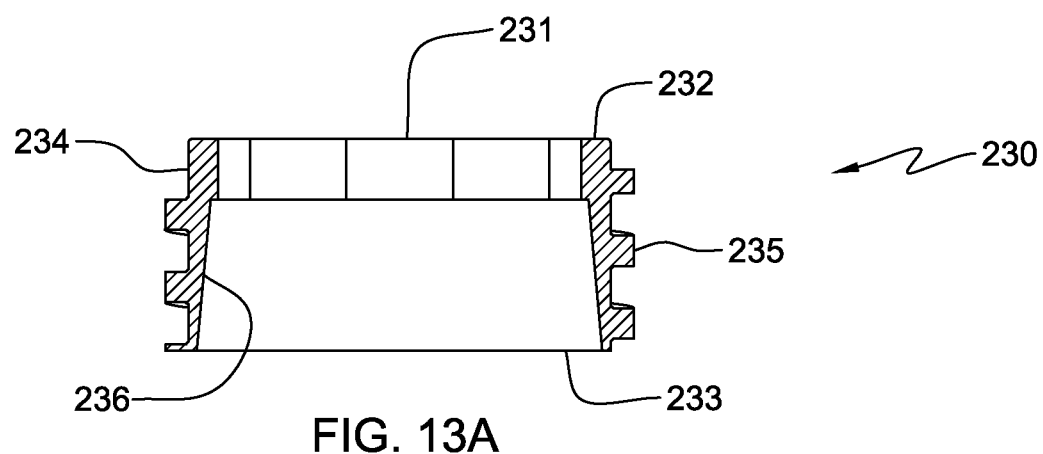
FIG. 13A is an enlarged sectional view of a compression member of the pedicle screw assembly of FIG. 6, in accordance with an aspect of the present invention.

FIGS. 6 and 13A show compression member 230 has being generally cylindrical in nature, with a through hole 231 at the center. Through hole 231 would permit the use of a drive or removal instrument to pass through compressive member 230 and interface directly with bone fastener 270. As shown in FIG. 6, hole 231 has central projecting features that may be used to engage a driver that is used to rotate compression member 230 during insertion into receiving housing 250. Compression member 230 also includes an upper or top surface 232 that will contact the bottom aspect of an elongated member when assembly 200 is constructed. Top surface 232 is seen in FIGS. 6 and 13A as being planar. It is further contemplated that, although not shown, top surface 232 may include a depression to form an arcuate surface that will result in more surface contact between compression member 230 and an elongated member when assembly 200 is loaded by set screw 210. The sectional view seen in FIGS. 10 and 13A show that the lower or bottom surface 233 of compression member 230 as being generally planar. The planar orientation facilitates the seating of compression member 230 within the central bore 251 of receiving housing 250.

Also seen in FIG. 13A is the conical inner surface 236 of compression member 230. Conical inner surface 236 includes a draft angle that corresponds to the taper angle of the outer surface 242 of locking member 240. Conical inner surface 236 is designed and configured to interact and engage with conical outer surface 242 of locking member to facilitate the load transfer between these two elements when a compressive force is applied by the tightening of set screw 210 during the assembly process. The taper angles of conical inner surface 236 and conical outer surface 242 allow for surface contact between the two elements when seated relative to each other and diminish potential point loading.

Compression member 230 has a cylindrical outer surface 234 that includes threads 235. Compression member 230 is initially threaded through the threads 256 located in the proximal end 252 of receiving housing 250. After compression member 230 is threaded past threads 256, compression member is advanced into the intermediate portion 257 of receiving housing 250 that includes a retention mechanism 259. Retention mechanism 259 is positioned on the inner surface 258 of intermediate portion 257 of receiving housing 250. (See FIG. 11B). For example purposes, retention mechanism 259 is shown in the form of at least one corresponding thread onto which compression member 230 may be threaded. The purpose and functionality of retention member 259 will be discussed in more detail below.

Figure 13B:
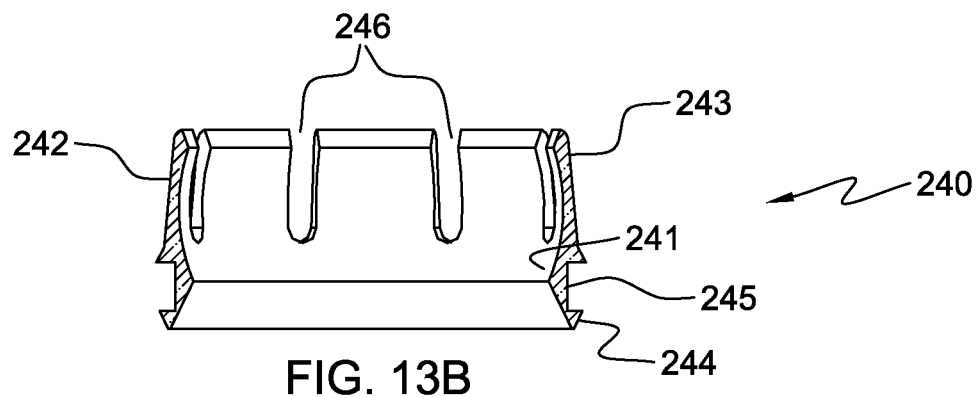
FIG. 13B is an enlarged sectional view of the locking member of the pedicle screw assembly of FIG. 6, in accordance with an aspect of the present invention.

FIGS. 6, 10 and 13B show locking member 240, which functions to encapsulate and hold the spherical head 271 of bone fastener 270 when a compressive load is applied to compression member 230. As seen in FIG. 13B, the inner surface 241 of locking member 240 is for example purposes, spherically shaped relative to the central axis of assembly 200. Spherical inner surface 241 is configured to mate with the corresponding spherical head 271 of bone fastener 270. As noted above, both inner surface 241 and head 271 may also have alternative shapes to address certain clinical situations in which assembly 200 is used. The outer surface 242 of locking member 240 in the proximal portion 243 is conically shaped to match the conically shaped inner surface 236 of compression member 230 when the two components are mated together. Conical outer surface 242 tapers out from the top aspect to the bottom aspect of locking member 240, such that the top edge of conical outer surface 242 is smaller in diameter than the bottom edge of conical outer surface 242.

A circumferential groove or notch 245 is seen in FIG. 13B in the distal portion 244. Groove 245 will engage with a corresponding distal flange 261 positioned proximate to the first or distal opening 254 of receiving housing 250. Groove 245 in combination with flange 261 will likely function to keep locking member 240 from falling through first opening 254 and out of central bore 251. Locking member 240 is generally anticipated to be a single component with material removed in multiple locations to permit elastic deformability, which may be expandability or compressibility. More specifically, as seen in FIGS. 6 and 13B, proximal portion 243 includes a plurality of vertically oriented slots 246 that allow for the elastic expansion of spherical inner surface 241 when spherical head 271 is advanced into locking member 240 from a distal or bottom to proximal or top direction. One skilled in the art will appreciate that such expansion of locking member 240 may be accomplished by other mechanical means through other various oriented relief placement, as well as by fabricating locking member 240 out of a tough and elastically deformable material. The deformability of proximal portion 243 and spherical inner surface 241 allows locking member 240 to receive a larger diameter head than the non-expanded sized spherical inner surface 241. Having the ability to expand will facilitate maximum surface contact between spherical inner surface 241 and spherical head 271 following placement within locking member 240.

Figure 7:
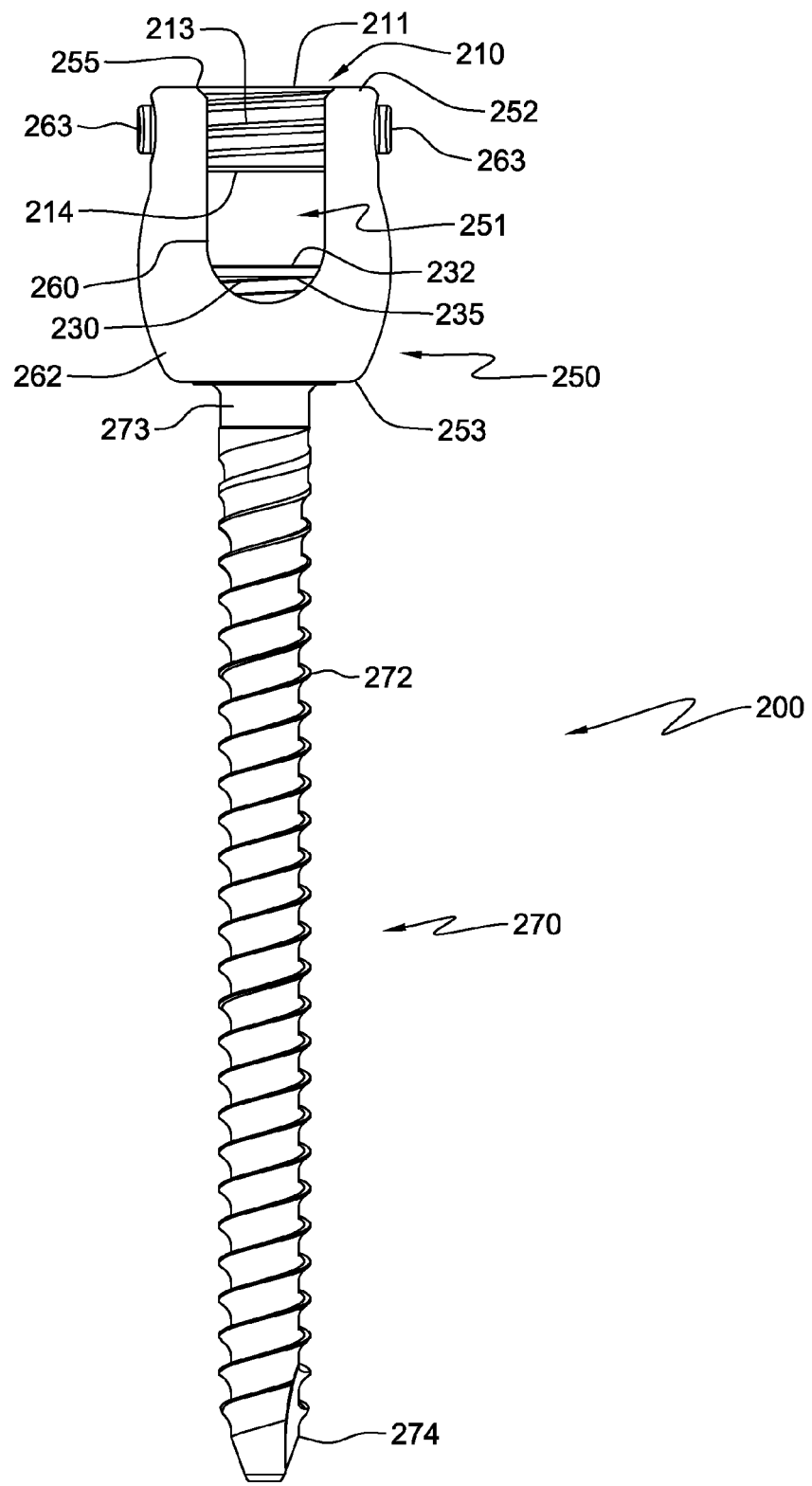
FIG. 7 is a side view of the pedicle screw assembly of FIG. 6, in accordance with an aspect of the present invention.
Figure 8:
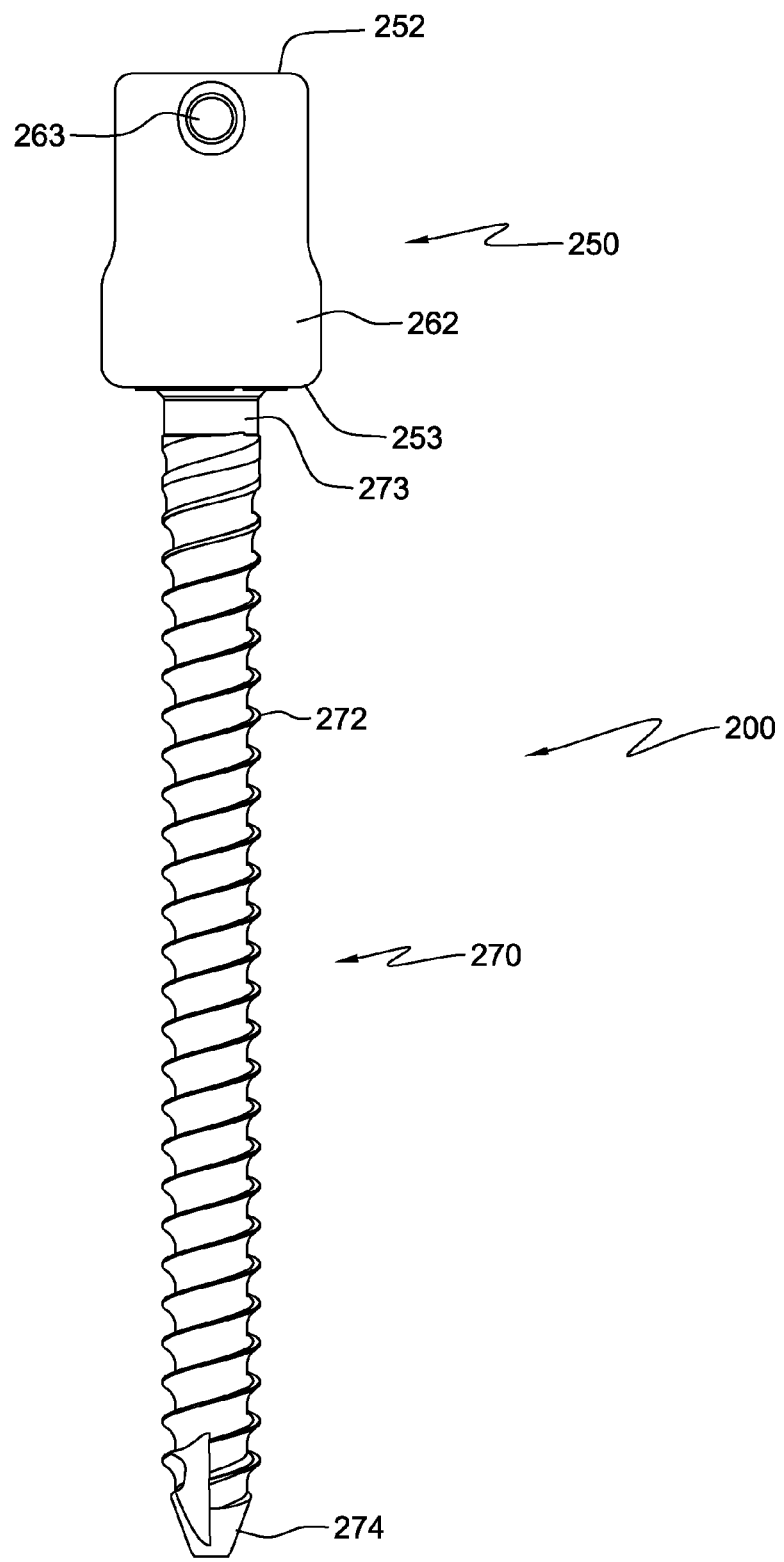
FIG. 8 is a lateral view of the pedicle screw assembly of FIG. 6, in accordance with an aspect of the present invention.

As seen in FIGS. 7 and 8, receiving housing 250 has a generally tulip-like shaped outer profile with at least two horizontally oriented bosses 263 extending away from the outer surface 262. Bosses 263 are oriented to facilitate the connection of an insertion instrument that may be using during an open or minimally invasive surgical procedure.

Figure 11B:
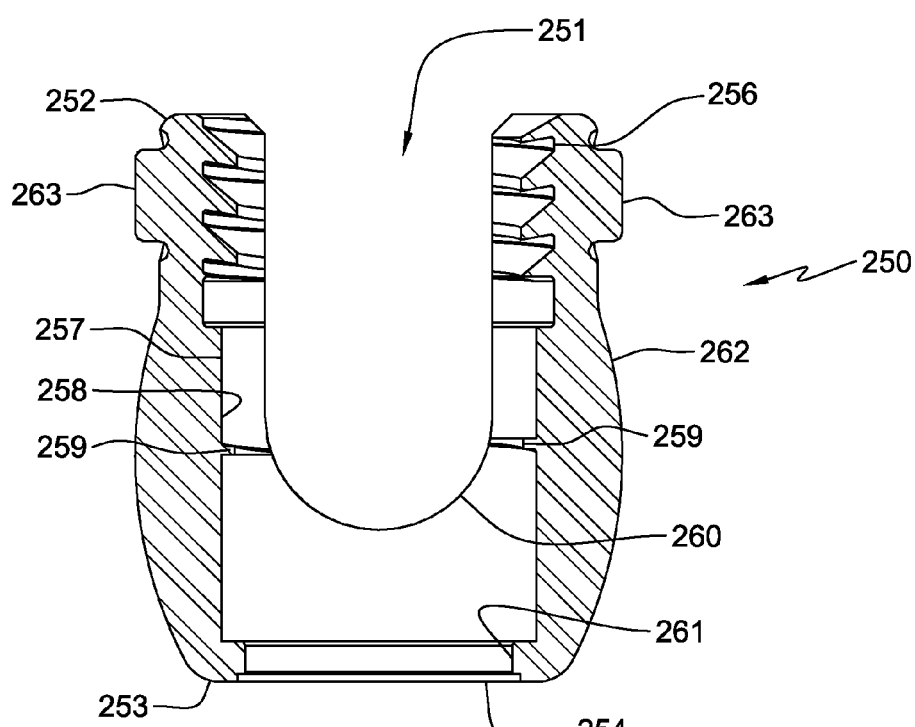
FIG. 11B is an enlarged sectional view of the receiving housing of the pedicle screw assembly of FIG. 6, in accordance with an aspect of the present invention.

FIGS. 10 and 11B are sectional views of receiving housing 250 and show central bore 251 extending from the proximal end 252 to the distal end 253. First or distal opening 254 is a hole that is located at the bottom or distal end 253 and is generally sized to receive spherical head 271 when assembly 200 is being constructed. A second or proximal opening 255 is located at proximal end 252 and is configured to receive locking member 240, compression member 230, an elongated member and set screw 210.

Oriented perpendicular to central bore 250 is transverse U-shaped channel 260 that extends from one outer side of receiving housing 250 to the opposite outer side. U-shaped channel 260 is configured to receive the elongated member.

Also shown in FIGS. 10 and 11B are threads 256 which are located on the inner surface of central bore 251 in proximal end 252. Threads 256 are the same as the corresponding threads 213 of set screw 210, which for example purposes are shown to be buttress threads. Threads 256 extend for a limited length within central bore 251 to avoid possible interference with the inserted elongated member after it has been seated at the base of U-shaped channel 260. Intermediate portion 257 extends between proximal end 252 and distal end 253 and has a smooth inner surface 258 to facilitate the placement of compression member 230 and locking member 240 within central bore 251. Disposed on inner surface 258 is retention mechanism 259 that is shown in FIG. 11B, for example purposes, to be a single thread. Retention mechanism 259 will function to keep compression member 230 positioned in distal end 253 of receiving housing 250 when low or no compressive loads are being applied by set screw 210. In operation, locking member 240 is advanced first through second opening 255 and into central bore 251 before moving to a position in distal end 253. Compression member 230 typically has a larger threaded outer diameter than locking member 240 is then threaded through threads 256 and advanced into intermediate portion 257. Compression member 230 is then threaded over retention mechanism 259 to a position below or more distal to retention mechanism 259. The thread(s) that comprise retention mechanism 259 inhibits compression member 230 from moving above retention member 259.

As seen in FIG. 11B, a centrally protruding circumferential distal flange 261 is located proximate to first or distal opening 254. Flange 261 engages with external groove 245 of locking member 240 to securely seat locking member 240 at distal end 253 of receiving housing 250.

FIG. 6 further shows bone fastener 270 before insertion into first opening 254 of receiving housing 250. For example purposes, bone fastener 270 is shown as a bone screw, although one skilled in the art will appreciate that many different types of bone fasteners may be used, including but not limited to pins, rods and hooks. Bone fastener 270 has a proximal end 273 and a distal end 274 with an intermediate threaded portion 272. Threaded portion 272 typically will have cancellous threads. Distal end 274 may also include a self-tapping tip to facilitate insertion into the bone. Bone fastener 270 also includes a spherical head 271 that extends from proximal end 273. Included within spherical head 271 may be a female or internal drive opening 275 that receives a tip of a screw driver or like insertion tool. The configuration of internal drive opening 275 may be for example purposes, a hex or hex lobe. Spherical head 271 also has a spherical outer surface 277. Surface 277 will typically be textured or roughened in some manner, including have a blast finish or slight circumferential ridges. The surface texturing assists with the securement of spherical head 271 within locking member 240 following placement of spherical surface 277 in contact with spherical inner surface 241 of locking member 240. As a result of the alignment of spherical head 271 within locking member 240, bone fastener 270 does not interact or come in contact with receiving housing 250 or the elongated member in any manner. As discussed above, alternate shapes may be used for both the head of bone fastener 270 and the inner surface of locking member 240. These shapes may be cylindrical, oval, conical, and tubular and may be used for certain clinical situations.

It would be understood by one skilled in the art that if an alternative shape was used, both the head and inner surface of the respective bone fastener 270 and locking member 240 would need to match each other.

As further shown in FIG. 10, bone fastener 270 may also have a central bore 276 that extends from proximal end 273 to distal end 274. Cannulation 276 is typically sized to accommodate guide wires and pins that may be used to facilitate insertion of bone fastener 270 in the target bone.

Generally, the pedicle screw assembly 100, 200 may be fabricated from well known biocompatible materials including metals, composites and polymers. Further, various parts of the assembly, including but not limited to, receiving housing 150, 250 set screw 110, 210 bone fastener 170, 270 may have grown nanosurfaces or applied nanocoatings which are configured to facilitate bone growth and/or reduce the colonization of bacteria or adjacent tissue inflammation. Such nanosurfaces or nanocoatings may have varying surface roughness, surface configurations and sized particles to accomplish these functionalities.

Figure 14:
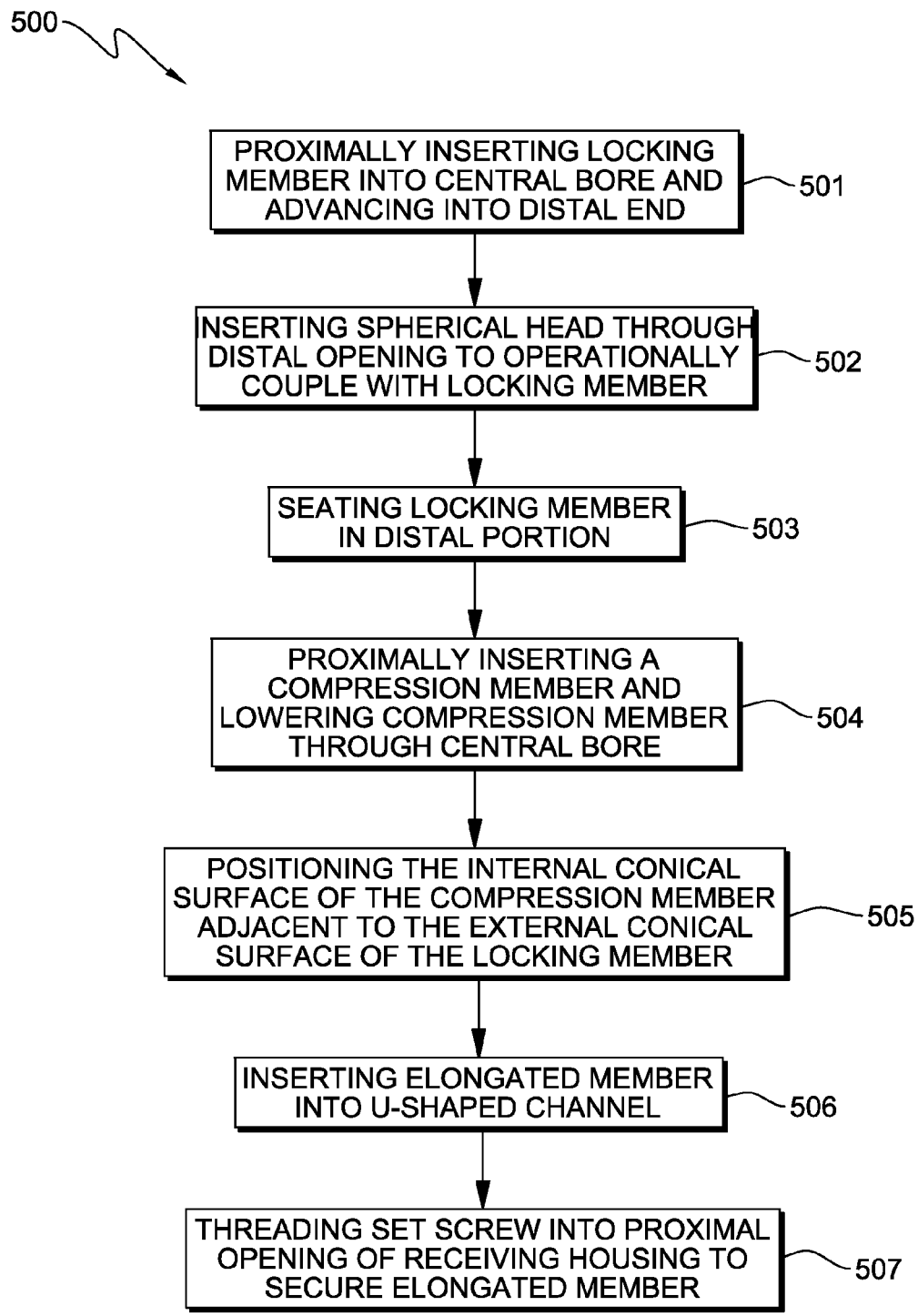
FIG. 14 is a flow chart showing the method of assembly of the pedicle screw system, in accordance with an aspect of the present invention.

A method of assembly 500 for the disclosed pedicle screw system is shown in FIG. 14. The method of assembly 500 results in reduced manufacturing costs, reduced in vivo locking torque requirements which in turn reduces the torsional stresses on the bone-bone screw implant site and provides for reduced component size profiles, resulting in a decrease in adjacent soft tissue complications.

The method of assembly 500 includes the step 501 of advancing locking member 140, 240 through proximal end 152, 252 of central bore 151, 251 and into distal end 153, 253 of receiving housing 150, 250. The method 500 may include the step 502 of inserting spherical head 171, 271 of the bone fastener 170, 270 through first or distal opening 154, 254 of receiving housing 150, 250 and advancing bone fastener 170, 270 into central bore 151, 251 far enough to couple spherical head 171, 271 with spherical inner surface 141, 241 of the locking member 140, 240. The method 500 may also include the step 503 of seating locking member 140, 240 in distal end 153, 253 proximate to first opening 154, 254 to prevent locking member 140, 240 from expanding and releasing the spherical head 171, 271.

The method of assembly 500 may further include the step 504 of inserting compression member 130, 230 proximally through second or proximal opening 155, 255 of receiving housing 150, 250 and lowering compression member 130, 230 through central bore 151, 251 to a location below retention mechanism 159, 259. Compression member 130, 230 may then be positioned above conical outer surface 142, 242 of locking member 140, 240. With the bone fastener relationship with the locking member maintained, method 500 may further still include the step 505 of pushing compression member 130, 230 distally in central bore 151, 251 of receiving housing 150, 250 such that conical outer surface 142, 242 of locking member 140, 240 is now adjacent to conical internal surface 136, 236 of the compression member 130, 230.

The method may also include the step 506 of inserting elongated member 120 into U-shaped transverse channel 160, 260. A next step 507 may be to thread set screw 110 into second opening 155, 255 of receiving housing 150, 250 and securing elongated member 120 in place by applying a compression load through elongated member 120 and continuing through to compression member 130, 230. The compressive load is then transferred onto locking member 140, 240 and spherical inner surface 141, 241 which results in the securement of the position of spherical head 171, 271 of bone fastener 170, 270. Because of the fixed position of locking member 140, 240 to compression member 130, 230 with the captured spherical head 171, 271 of bone fastener 170, 270, the surgeon will be able to make final positional adjustments prior to the final tightening of set screw 110, 210 onto the inserted elongated member 120.

Although the preferred embodiments have been depicted and described in detail herein, it will be apparent to those skilled in the relevant art that various modifications, additions and substitutions can be made without departing from its essence and therefore these are to be considered to be within the scope of the following claims.

The invention claimed is:

1. A pedicle screw assembly, comprising:
   a bone fastener having a head at a proximal end and a threaded portion extending between the proximal end and a distal end;
   a compression member having a cylindrical outer surface and a conical inner surface;
   a locking member having an outer surface adapted to mate with the conical inner surface of the compression member, wherein the outer surface of the locking member has a proximal portion and a distal portion with at least one of a circumferential flange and a circumferential groove, the proximal portion of the locking member further comprising a plurality of vertical slots, the slots extending from the outer surface to the inner surface and from a top of the proximal portion down to at least one of the circumferential flange and the circumferential groove in the distal portion, the slots being disposed around an outer circumference of the proximal portion, and wherein the locking member further comprises a relief extending from the outer surface to the inner surface and from a top of the proximal portion to a bottom of the distal portion; and
   a receiving housing having a central bore extending from a proximal end to a distal end, wherein the distal end comprises a first opening sized to receive the head of the bone fastener and the proximal end comprises a second opening sized to receive the locking member and the compression member, wherein the receiving housing further comprises an intermediate portion extending between the proximal end and the distal end, and wherein the intermediate portion further comprises a retention mechanism extending from the intermediate portion of the receiving housing inwardly towards the central bore;
   wherein the compression member is positioned below the retention mechanism and an uppermost surface of the compression member engages a bottommost surface of the retention mechanism of the receiving housing.

2. The pedicle screw assembly of claim 1, wherein the head of the bone fastener has a generally spherical shape.

3. The pedicle screw assembly of claim 2, wherein the locking member further comprises an inner surface, wherein the inner surface is configured to articulate with the generally spherical shape of the head.

4. The pedicle screw assembly of claim 1, wherein the compression member further comprises a top surface and a bottom surface, and wherein the top surface is at least one of planar and concave and the bottom surface is planar.

5. The pedicle screw assembly of claim 1, wherein the cylindrical outer surface of the compression member is smooth.

6. The pedicle screw assembly of claim 1, wherein the cylindrical outer surface of the compression member is threaded.

7. The pedicle screw assembly of claim 6, wherein the threads of the compression member are complimentary to interior threads at the proximal end of the receiving housing.

8. The pedicle screw assembly of claim 1, wherein the proximal portion of the outer surface of the locking member is conically shaped.

9. The pedicle screw assembly of claim 8, wherein the distal portion of the outer surface of the locking member is cylindrical.

10. The pedicle screw assembly of claim 1, wherein the locking member is deformable.

11. The pedicle screw assembly of claim 1, wherein the proximal end of the receiving housing has threads.

12. The pedicle screw assembly of claim 1, wherein the intermediate portion of the receiving housing has a cylindrical inner surface.

13. The pedicle screw assembly of claim 1,
wherein the retention mechanism comprises at least one of a thread and a barb disposed on an inner surface of the intermediate portion.

14. The pedicle screw assembly of claim 1, wherein the first opening of the receiving housing is smaller than the central bore.

15. The pedicle screw assembly of claim 1, wherein the first opening of the receiving housing is smaller than the compression member and the locking member.

16. The pedicle screw assembly of claim 1, wherein the locking member is configured to couple to the receiving housing adjacent to the first opening to maintain the position of the locking member within the receiving housing upon compression of the locking member.

17. The pedicle screw assembly of claim 1, further comprising a set screw having a threaded portion with exterior threads and a head portion, wherein the exterior threads of the threaded portion are complimentary to interior threads at the proximal end of the receiving housing.

18. The pedicle screw assembly of claim 1, wherein the receiving housing further comprises a plurality of hubs, the plurality of hubs extending substantially perpendicular from an outside surface of the receiving housing.

19. The pedicle screw assembly of claim 1, wherein the head of the bone fastener is one of a spherical, conical, tubular and oval shape.

20. A pedicle screw assembly, comprising:
a bone fastener having a head at a proximal end and a threaded portion extending between the proximal end and a distal end;
a compression member having a cylindrical outer surface and a conical inner surface;
a locking member having an outer surface adapted to mate with the conical inner surface of the compression member, wherein the outer surface of the locking member has a proximal portion and a distal portion with at least one of a circumferential flange and a circumferential groove, the proximal portion of the locking member further comprising a plurality of vertical slots, the slots extending from the outer surface to the inner surface and from a top of the proximal portion down to at least one of the circumferential flange and the circumferential groove in the distal portion, the slots being disposed around an outer circumference of the proximal portion;
an elongated member;
a set screw having a threaded portion and a head portion having an internal drive opening; and
a receiving housing having a central bore extending from a threaded proximal end to a distal end and a U-shaped cavity defined by an outer surface of the receiving housing and configured to receive the elongated member, wherein the distal end comprises a first opening sized to receive the head of the bone fastener and the proximal end comprises a second opening sized to receive the locking member and the compression member, wherein the set screw is threadingly engaged to the threaded proximal end to apply a compressive load to the elongated member, whereby the compressive load is transmitted onto the compressive member and the locking member to fix the bone fastener in a position relative to the receiving housing, wherein the receiving housing further comprises an intermediate portion extending between the proximal end and the distal end, and wherein the intermediate portion further comprises a retention mechanism extending from the intermediate portion of the receiving housing inwardly towards the central bore;
wherein the compression member is positioned below the retention mechanism and an uppermost surface of the compression member engages a bottommost surface of the retention mechanism of the receiving housing.

21. A method of assembly of a pedicle screw system, comprising:
proximally inserting a locking member into a central bore of a receiving housing wherein the locking member comprises an outer surface with a proximal portion and a distal portion having at least one of a circumferential flange and a circumferential groove, the proximal portion further comprising a plurality of vertical slots, the slots extending from the outer surface to the inner surface and from a top of the proximal portion down to at least one of the circumferential flange and the circumferential groove in the distal portion, the slots being disposed around an outer circumference of the proximal portion and open towards a proximal end of the receiving housing;
inserting a head of a bone fastener through a distal opening of the central bore of the receiving housing to operationally couple with the locking member;
seating the locking member in a distal portion of the central bore proximate to the distal opening;
proximally inserting a compression member into the central bore of the receiving member; and
positioning an internal conical surface of the compression member adjacent to an external conical surface of the locking member, wherein an uppermost surface of the compression member is positioned below a retention mechanism disposed on an inner wall of the receiving housing and extends from the inner wall of the receiving housing in towards the central bore.

22. The method of claim 21, wherein the compression member detachably engages the retention mechanism to securely retain the compression member in the distal portion of the central bore, and wherein a top surface of the compression member engages a bottom surface of the retention mechanism of the receiving housing.

23. The method of claim 21, wherein an elongated member is inserted into a u-shaped transverse channel in the receiving housing to contact a top surface of the compression member.

24. The method of claim 21, wherein a retaining member is coupled to a proximal portion of the central bore to apply a compressive force to the elongated member to secure the bone fastener position within the distal opening of the receiving housing.

* * * * *